United States Patent [19]

Yamazaki et al.

[11] Patent Number: 4,902,802

[45] Date of Patent: Feb. 20, 1990

[54] PROCESS FOR PREPARING PYRIDINE HOMOLOGUES BY MEANS OF SUBSTITUTED CYCLOPENTADIENYL COBALT COMPLEXES

[75] Inventors: Hiroshi Yamazaki, Kamifukuoka; Yasuo Wakatsuki, Shiki, both of Japan

[73] Assignees: Denki Kagaku Kogyo Kabushiki Kaisha, Chiyoda; Rikagaku Kenkyusyo, Wakoh, both of Japan

[21] Appl. No.: 942,815

[22] Filed: Dec. 22, 1986

Related U.S. Application Data

[60] Division of Ser. No. 818,065, Jan. 13, 1986, Pat. No. 4,656,299, which is a continuation of Ser. No. 547,712, Nov. 1, 1983, abandoned.

[30] Foreign Application Priority Data

Nov. 6, 1982 [JP] Japan ................................ 57-193951
Jun. 9, 1983 [JP] Japan ................................ 58-101721
Jun. 9, 1983 [JP] Japan ................................ 58-101722

[51] Int. Cl.$^4$ .................. C07D 213/09; C07D 213/10; C07D 213/12
[52] U.S. Cl. .................................... 546/251; 546/250; 546/253; 546/254
[58] Field of Search ................ 546/250, 251, 253, 254

[56] References Cited

U.S. PATENT DOCUMENTS 4,267,329  5/1981  Bonnemann et al. .................... 546/4
4,469,638  9/1984  Bonnemann et al. ................. 556/12

Primary Examiner—Alan L. Rotman
Attorney, Agent, or Firm—Oblon, Spivak, McClelland, Maier & Neustadt

[57] ABSTRACT

A complex of an electron attracting group-substituted $\eta^5$-cyclopentadienylcobalt with a polyene or an acetylene.

41 Claims, No Drawings

PROCESS FOR PREPARING PYRIDINE HOMOLOGUES BY MEANS OF SUBSTITUTED CYCLOPENTADIENYL COBALT COMPLEXES

This is a divisional of U.S. Ser. No. 818,065, filed Jan. 13, 1986, now issued as U.S. Pat. No. 4,656,299, which is a continuation of Ser. No. 06/547,712 filed 11-01-83 abandoned.

BACKGROUND OF THE INVENTION

The present invention relates to a novel complex of an electron attracting group-substituted $\eta^5$-cyclopentadienylcobalt with a polyene or an acetylene, and a process for preparing a pyridine homologue from an alkyne and a nitrile by using the complex as a catalyst.

Description of the Prior Art

Cyclopentadienylcobalt cyclic diene complexes and their use as catalysts for the synthesis of a substituted pyridine from an alkyne and a nitrile, have already been known. For instance, cycloalkadienylcobalt cycloalkadiene complexes and their use as catalysts for the cyclization of two molecules of an alkyne and one molecule of an nitrile at the respective triple bond portions to form a substituted pyridine, have been known (Japanese Unexamined Patent Publications No. 135084/1975 and No. 25780/1977 and U.S. Pat. No. 4,267,329). However, these catalysts do not provide an adequate catalytic activity.

A synthesis of pyridine or its homologues by reacting an alkyne with a nitrile to co-cyclize them at their triple bonds a single step is a superb process. Some of the present inventors have previously disclosed that a cobalt compound, particularly an $\eta^5$-cyclopentadienylcobalt derivative, is an effective catalyst for such a reaction (Japanese Examined Patent Publications No. 13153/1976 and No. 15597/1977). However, a catalyst having a still higher catalytic activity has been desired.

As a highly active catalyst for such a reaction, it has been proposed to use a borabenzene cobalt complex (Éuopean Patent No. 64268). However, this catalyst has drawbacks that its preparation is cumbersome and it is very expensive.

It is accordingly an object of the present invention to provide a highly active catalyst which can readily be prepared and is useful for the synthesis of a pyridine homologue from an alkyne and a nitrile.

As a result of extensive researches, the present inventors have found that a cobalt complex having an electron attractive substituent on its cyclopentadienyl ring exhibits a superior catalytic activity. The present invention has been accomplished based on this discovery.

Thus, the present invention provides, as a novel compound, a complex of an electron attracting group-substituted $\eta^5$-cyclopentadienylcobalt with a polyene or an acetylene, and a process for preparing a pyridine homologue which comprises reacting an alkyne with a nitrile in the presence of the novel compound as the catalyst.

The novel complex of the present invention is represented by the general formula:

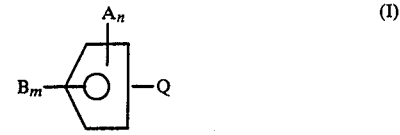

where A is a $C_1$-$C_4$ alkyl group and/or a phenyl group, n is an integer of from 0 to 2, B is an alkoxycarbonyl group in which the alkoxy moiety contains from 1 to 3 carbon atoms or a $C_1$-$C_4$ acyl group, m is an integer of 1 or 2, and Q is —Co=$R_1$ (where $R_1$ is a $C_4$-$C_{12}$ polyene having from 2 to 4 double bonds, which is unsubstituted or substituted by from 1 to 4 substituents selected from the group consisting of a $C_1$-$C_4$ alkyl group, a $C_1$-$C_4$ alkoxycarbonyl group, a phenyl group, a cyano group and a cyanomethylene group and which forms a coordinate bond with the cobalt atom at its diene portion, provided $R_1$ excludes a polyene composed solely of an aromatic ring),

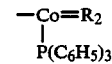

(where $R_2$ is an organic residue of a metallo-cyclic cyclopentadiene which is unsubstituted or substituted by from 1 to 4 substituents selected from the group consisting of a $C_1$-$C_4$ alkyl group, a $C_1$-$C_4$ alkoxycarbonyl group, a phenyl group and a cyano group),

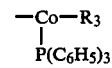

(where $R_3$ is an acetylene which is substituted by one or two substituents selected from the group consisting of a $C_1$-$C_4$ alkyl group, a $C_1$-$C_4$ alkoxycarbonyl group, a phenyl group and a cyano group and which forms a coordinate bond with the cobalt atom at its triple bond portion), or

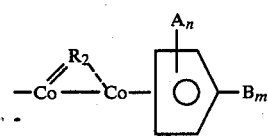

(where $R_2$, A, B, n and m are as defined above).

It used to be difficult to prepare a substituted $\eta^5$-pentadienyl cobalt complex having an electron attracting substituent on its cyclopendadienyl ring. The present inventors have solved the difficulty by developing the following novel methods for its preparation.

(i) A method in which an alkoxycarbonyl- or acyl-substituted cyclopentadienyl alkali metal complex is reacted with a tris-triphenylphosphine cobalt monohalogenide, followed by a reaction with a polyene or an acetylene to obtain the desired complex.

(ii) A method in which an alkoxycarbonyl- or acyl-substituted cyclopentadienyl alkali metal complex, a cobalt (II) halide and a polyene or an acetylene, are reacted in the presence of a reducing agent.

In the process for the synthesis of pyridine or its homologue by reacting an alkyne with a nitrile, the complex of an electron attracting group-substituted cyclopentadienylcobalt with a polyene or an acetylene exhibits an extremely high catalytic activity. Especially, the complex having an alkoxycarbonyl group or an acyl group as the electron attractive substituent, is particularly effective to provide a far superior reaction rate as compared with conventional catalysts of this type, and its catalytic efficiency is as high as from 1.5 to 20 times that of the conventional catalysts. Further, it effectively serves to suppress the formation of aromatic hydrocarbons as by-products of the reaction to a level of at most 1/10. Furthermore, by virtue of the high catalytic activity of the complex, it is possible to substantially reduce the pressure for the reaction. This is extremely effective to prevent decomposition or explosion when a lower acetylene is used as the starting material. Thus, this is very important for an industrial application.

The general formula I covers the following types of complexes:

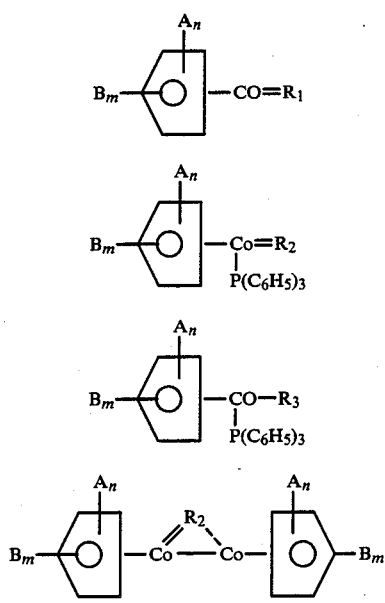

In the formulas II to V, A, B, n, m, $R_1$, $R_2$ and $R_3$ are as defined above with respect to the general formula I. The complex of the formula III is a substance in which two molecules of acetylene or its derivative ($R_2'$) are reacted, and the triple bond portion of the acetylene in the reaction product forms together with cobalt a metallocyclic cyclopentadiene ring, and triphenylphosphine forms a coordinate bond with cobalt. The complex of the formula V has a structure in which instead of the triphenylphosphine in the formula III, a substituted $\eta^5$-cyclopentadienylcobalt is bonded to form a cobalt-cobalt bond, which further establishes a diene coordination with the cobaltacyclopentadiene ring.

The polyene to be used in the present invention may be selected from a wide range of polyenes. For instance, there may be mentioned butadiene, isoprene, or cyclopentadiene, dicyclopentadiene, hexadiene, norbornadiene, indene, cyclooctadiene, cyclooctatetraene, azulene, cyclododecatriene, or alkyl- or phenyl-substituted derivatives thereof or alkoxy- carbonyl-, cyano- or cyanomethylene-substituted derivatives thereof. However, polyenes composed solely of an aromatic ring such as benzene, toluene or xylene are not useful for the present invention as they are not reactive.

As the acetylene to be used in the present invention, there may be mentioned acetylene, methylacetylene, ethylacetylene, hexadiyne, phenylacetylene, or alkoxycarbonyl- or cyano-substituted derivatives thereof.

The complexes of the present invention are all novel compounds, and their structures have been ascertained by elementary analysis, infrared spectrum, and NMR.

The unsubstituted or substituted $\eta^5$-alkoxycarbonyl- or $\eta^5$-acyl-cyclopentadienylcobalt complexes of the present invention have been found to exhibit an extremely high catalytic activity when used as catalysts for the synthesis of an unsubstituted or substituted pyridine from an alkyne and a nitrile. Cycloalkadienylcobalt complexes usually have a catalytic activity for the synthesis of pyridine derivatives by co-cyclization reaction of an alkyne and a nitrile. However, cyclopentadienylcobalt complexes having an electron attracting substituent on its cyclopentadienyl ring have a higher catalytic activity.

The unsubstituted or substituted $\eta^5$-alkoxycarbonyl- or $\eta^5$-acyl-cyclopentadienylcobalt complexes of the present invention exhibit especially good catalytic activity.

When the catalyst is used in an amount of at least 0.1 mmol/liter in the reaction system, an effective catalytic activity is obtainable. It is usually unnecessary to bring the concentration higher than 100 mmol/liter.

The starting materials may be selected from wide ranges of alkynes and nitriles when the catalyts of the present invention are used, like in the cases where conventional catalysts are used.

As the alkynes, there may be employed acetylene, a mono substituted alkyne such as an alkyl-, alkenyl- or aryl-acetylene, a di-substituted acetylene such as a dialkyl-, diaryl-, alkyl-alkenyl- or alkyl-aryl-acetylene, or a mixture of such alkynes. Further, an ether- or alcohol-derivative thereof may also be used.

On the other hand, as the nitriles, there may be advantageously employed a mononitrile such as hydrogen cyanide or an alkyl-, aryl- or alkenyl-nitrile, or a polyfunctional nitrile having a plurality of nitrile groups.

The molar ratio of the alkyne to the nitrile may be optionally selected within a range of from 0.01 to 100. However, in order to minimize the formation of by-products, it is preferred that the nitrile is used in excess of the amount of the alkyne.

The process of the present invention may be conducted in such a manner that the catalyst is added to a nitrile in the presence or absence of a solvent, and an alkyne is added at a temperature of from 15° to 200° C., whereby the reaction will proceed. As the solvent, there may be used a variety of solvents such as an aromatic hydrocarbon, an alcohol, an amine, an ether, an ester or an alkylcarboxyamide. However, such a solvent is not necessarily required since the starting material nitrile serves as a solvent.

The complex obtained according to the present invention may be used for the synthesis of a pyridine homologue without isolation or purification before use. This is extremely advantageous for the practical application of the catalyst to an industrial operation.

The feature of the process of the present invention is that the catalytic activity and the reaction rate are high.

Another important feature is that it is thereby possible to substantially reduce aromatic hydrocarbons which are likely to form as by-products in the synthesis of the pyridine homologues. Accordingly, it is readily possible to attain the productivity and the concentration of the product which adequately satisfy the industrial requirements.

Especially when a lower alkyne such as acetylene is used as a starting material, it is possible to conduct the reaction at a pressure substantially lower than that of the conventional reaction system, i.e. under pressure of from 0 to 30 kg/cm$^2$G, preferably from 5 to 20 kg/cm$^G$ and at an adequately practical reaction rate. This is practically very important in that the lower alkyne is likely to lead to decomposition or explosion when pressurized.

It may be said that it has been made possible for the first time by the present invention to produce readily and in an industrial scale an industrially important product such as vinyl pyridine, α-picoline or pyridine from acetylene and a nitrile.

Heretofore, an $\eta^5$-cyclopentadienylcobalt polyene complex has been usually prepared by reacting dicarbonyl- $\eta^5$-cyclopentadienylcobalt with a polyene or an acetylene [Shin Jikken Kagaku Koza Vol. 12, pages 189-190 (Maruzen)]. However, according to such a conventional process, it has been difficult to produce an electron attracting group-substituted $\eta^5$-cyclopentadienylcobalt polyene complex and an electron attracting group-substituted substituted $\eta^5$-cyclopentadienylcobalt monoyne complex of the present invention. As a result of extensive researches, the present inventors have found novel methods for the synthesis. The present invention has been accomplished by this discovery.

The $\eta^5$-alkoxycarbonyl- or $\eta^5$-acyl-cyclopentadienylcobalt complex of the present invention is prepared by the following routes.

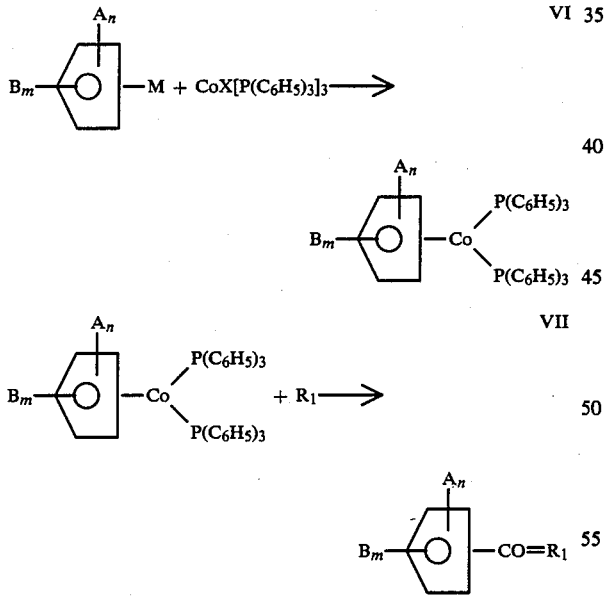

VI

VII

In the formula VI, M is an alkali metal and X is a halogen atom, and in the formula VII, R$_1$ is a C$_4$-C$_{12}$ polyene having from 2 to 4 double bonds, which is unsubstituted or substituted by from 1 to 4 substituents selected from the group consisting of a C$_1$-C$_4$ alkyl group, a C$_1$-C$_4$ alkoxycarbonyl group, a phenyl gorup, a cyano group and a cyanomethylene group. However, R$_1$ excludes a polyene composes solely of an aromatic ring. A is hydrogen or a C$_1$-C$_4$ alkyl group and/or a phenyl group, n is 0 to 2, B is an alkoxycarbonyl group in which the alkoxy moiety contains from 1 to 4 carbon atoms, or an acyl group, and m is 1 or 2.

Instead of the process of the formula VII, a process of the formula VIII may be employed.

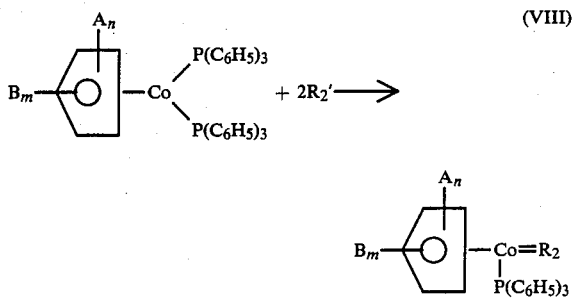

In the formula VIII, R$_2'$ is an acetylene which is unsubstituted or substituted by one or two substuents selected from the group consisting of a C$_1$-C$_4$ alkyl group, a C$_1$-C$_4$ alkoxycarbonyl group, a phenyl group and a cyano group, and R$_2$ is an organic residue of a metalocyliccyclopentadiene, which is composed of 2 molecules of R$_2'$ and a cobalt atom, which may have the same substituents as R$_2'$.

Instead of the process of the formula VII, a process of the formula IX may be employed.

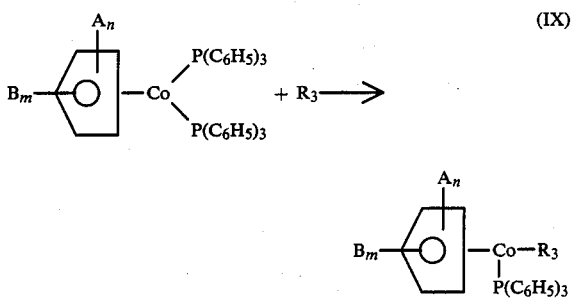

In the formula IX, R$_3$ is a substituted acetylene having the same substituents as R$_2'$.

Instead of the process of the formula VII, a process of the formula X may be employed,

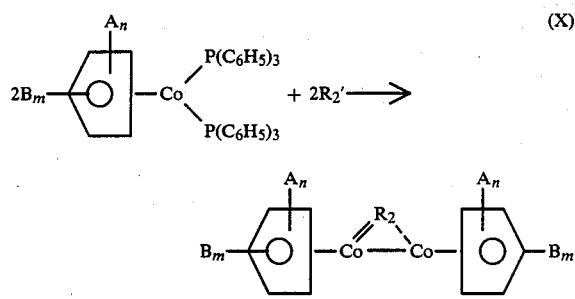

In the formula X, R$_2'$ and R$_2$ are as defined above with respect to the formula VIII. Instead of the triphenylphosphine in the formula VIII, a substituted $\eta^5$-cyclopentadienylcobalt is bonded to form a cobalt-cobalt bond, which further establishes a diene coordination with the cobaltacyclopentadiene ring.

The starting material of the formula VI such as an alkoxycarbonyl- or acyl-cyclopentadienyl sodium may be obtained by the process of Rausch [J. Am. Chem. Soc., 102, 1196 (1980)].

The alkoxycarbonyl group or the acyl group represented by B includes a methoxycarbonyl group, an ethoxycarbonyl group, an isopropoxycarbonyl group, a formyl group, an acetyl group, a propionyl group or a butylyl group, and it is synthesized respectively from the corresponding carbonate, chloroformate or carboxylate and a cyclopentadienyl alkali metal complex.

The introduction of an alkyl group and/or a phenyl group may be conducted by a conventional method, for instance, by reacting an alkali metal complex such as a cyclopentadienyl sodium with a corresponding halogenated alkyl or phenyl, and, if necessary, repeating this reaction. This reaction is preferably conducted prior to the introduction of the B group.

The tris-triphenylphosphine cobalt monohalogenides may readily be obtained by reacting a cobalt halide with triphenylphosphine in the presence of a reducing agent [Inorg. Chim. Acta., 3, 227 (1969)].

The reaction of the formula VI may be conducted by reacting a substantially equimolar amount or a slight excess thereof of an alkoxycarbonyl- or acyl-cyclopentadienyl alkali metal complex in a solvent at a temperature of from 0° to 80° C. for 24 hours. The reaction product thereby obtained may be isolated and purified, but may directly be used for the subsequent reaction without such isolation or purification. The reactions of the formulas VII, VIII, IX and X may be conducted by adding a polyene or an acetylene corresponding to the desired substance to the reaction solution of the formula VI and reacting the mixture at a temperature of from 0° to 150° C. for from 0.5 to 24 hours.

These reactions may preferably be conducted in an inert atmosphere free from the presence of oxygen. After concentrating tthe reaction product solutions, the reaction products may be isolated or purified by column chromatography.

The substituted $\eta^5$-cyclopentadienylcobalt polyene complexes thus obtained are stable in air.

A feature of the present invention resides in that a cyclopentadienyl alkali metal complex wherein one or two hydrogen atoms on the ring are substituted by an alkoxycarbonyl group or an acyl group, is used as a starting material, and the starting material is reacted with a tris-triphenylphosphine cobalt monohalogenide and the reaction product solution is directly reacted with a corresponding polyene or acetylene. The reaction of the formula VI has been known wherein a cyclopentadienyl sodium is used as a starting material. However, an alkoxycarbonyl- or acyl-cyclopentadienyl alkali metal complex has been used as the starting material for the first time by the present invention. Furthermore, the reaction of this reaction product with a polyene or an actylene has not been known before.

The $\eta^5$-alkoxycarbonyl-, and $\eta^5$-acyl-cyclopentadienylcobalt complexes represented by the general formula II may also be prepared by the following method.

Namely, (i) at least one of substituted cyclopentadienylcobalt monohalogenides represented by the formula XI:

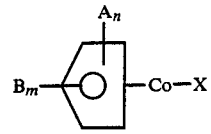

where A, B, X, m and n are as defined above, with respect to the formula XI, and (ii) at least one of $C_1$–$C_{16}$ polyenes having from 2 to 4 double bonds, excluding a polyene composed solely of an aromatic ring, are mixed, and the mixture is reacted with (iii) a reducing agent, whereby an electron attracting group-substituted $\eta^5$-cyclopentadienylcobalt-$\eta^4$-polyene complex of the formula II is prepared.

Alternatively, (i) at least one of substituted cyclopentadienyl alkali metal complexes of the formula VI, and (ii) at least one of cobalt(II) halide, are mixed and reacted to form a corresponding $\eta^5$-substituted cyclopentadienylcobalt monohalogenide, and without isolation or separation, this reaction product is directly reacted with (iii) at least one of $C_4$–$C_{16}$ polyenes having from 2 to 4 double bonds, excluding a polyene composed solely of an aromatic ring, in the presence of (iv) a reducing agent to obtain an electron attracting group-substituted $\eta^5$-cyclopentadienylcobalt-$\eta^4$-polyene complex of the formula II. In this process, the polyenes (iii) may be present at the time of the reaction of the reactants (i) and (ii).

cyclopentadienylcobalt monohalogenides are known compounds. Whereas, the substituted cyclopentadienylcobalt monohalogenides of the present invention are all novel compounds. The substituted cyclopentadienylcobalt monohalogenide may be prepared by reacting a substituted cyclopentadienyl alkali metal complex of the formula VI with a cobalt(II) halide. It has been found that in this case, it is important to react the two reactants in a ratio close to equimolar amounts as far as possible. If the amount of the cobalt salt is too small, by-products of cobaltcene type tend to increase. On the other hand, if the amount is excessive, unreacted substances tend to increase. The reaction may readily be carried out in the presence of a solvent at a temperature of from −20° to 50° C. As the solvent, an inert solvent such as a hydrocarbon or an ether may preferably be used. However, the above-mentioned polyene may be used as a solvent. From the reaction product solution thus obtained, the substituted cyclopentadienylcobalt mono-halogenide may be isolated. However, the reaction solution may directly be used for the subsequent reaction.

It has been found that the substituted cyclopentadienylcobalt monohalogenide and the polyene can readily be converted by the action of a reducing agent to a substituted cyclopentadienylcobalt polyene complex. Heretofore, it has been known to obtain a catalyst active for the synthesis of a pyridine derivative by reacting a cobalt salt with an alkyne or a nitrile in the presence of a reducing agent. However, it has not been known to use a substituted cyclopentadienylcobalt monohalogenide as the starting material, as in the present invention. The process for preparing a substituted cyclopentadienylcobalt polyene complex readily and in good yield has been found for the first time by the present invention.

The molar ratio of the substituted cyclopentadienylcobalt monohalogenide and the polyene is within a range of from 1 to 200. As the reducing agent, there may be used an alkali metal amalgam, hydride, borohydride, aluminum hydride, an alkyl aluminum or an alkyl zinc. The amount of the reducing agent is preferably at least equivalent to the amount of cobalt. The reaction is conducted at a temperature within a range of from −20° to 100° C. in the presence or absence of a solvent.

As the solvent, a hydrocarbon or an ether may preferably be used. The polyene as a reactant or the solution system of the preceeding step may be employed for this reaction. The reaction is preferably conducted in an inert atmosphere containing no oxygen, moisture or acidic gas under atmospheric pressure or elevated pressure. The reaction time may vary depending upon the temperature and the solvent, but is usually within 1 hour.

From the reaction product solution thus obtained, a pure product of the substituted $\eta^5$-cyclopentadienyl-cobalt-$\eta^4$-polyene complex may be obtained. This isolation operation can more readily be conducted than the isolation operation of the above-mentioned system wherein triphenylphosphine is used. However, when the complex is used as a catalyst for the process of the present invention, such an isolation operation is not necessarily required, and the reaction product solution may be used as it is. This system is particularly advantageous as compared with the above-mentioned system wherein is used triphenylphosphine, since the expensive isolation operation is not required.

Now, the present invention will be described in further detail with reference to Examples. However, it should be understood that the present invention is by no means restricted by such specific Examples.

EXAMPLES 1 TO 24

Various complexes of $\eta^5$-alkoxycarbonyl- and $\eta^5$-acylcyclopentadienylcobalt with polyenes or acetylenes were prepared. The preparation conditions are shown in Table 1, the data for the determination of the structures are shown in Table 2, and the structures of the complexes are shown in Table 3.

The preparation of typical complexes will be described below.

(i) Preparation of $\eta^4$-norbornadiene-$\eta^5$-methocycarbonyl cyclopentadienylcobalt Dimethyl carbonate (1.5 ml) was added to a tetrahydrofuran solution of cyclopentadienyl sodium (7 ml of a 2 mmol/ml solution), and the mixture was refluxed for 1 hour in a nitrogen atmosphere. The reaction solution thereby obtained was added to a suspension of tris-triphenylphosphine cobalt monochloride (8.81 g, 10 mmol) in benzene (20 ml). The color of the solution immediately turned red. To complete the reaction, the solution was stirred for a while and then norbornadiene (3 ml) was added and the mixture was refluxed for 1 hour on a hot water bath. After cooling, the reaction mixture was passed through a short alumina column to remove insoluble matters whereby a reddish orange solution eluted by benzene was collected. The solvent was distilled off by heating under reduced pressure. Hexane (20 ml) was added to the residue, and the mixture was left to stand overnight. The precipitated triphenylphosphine (4.64 g) was removed by decantation, and the red solution was again subjected to alumina chromatography. From the colorless solution eluted by hexane, triphenyphosphine (2.06 g) was further recovered. The solvent was distilled off under reduced pressure from the reddish orange solution eluted by benzene/hexane (1:1). The residue was dissolved in hexane under heating, and then left to stand in a refrigerator, whereby orange crystals (2.0 g, yield: 73%) were obtained.

(ii) Preparation of $\eta^4$-1,5-cyclooctadiene-$\eta^5$-acetylcyclopentadienyl cobalt In accordance with the Rausch method, 10 ml of a tetrahydrofuran solution of cyclopentadienyl sodium (20 mmol/10 ml THF) and 4 ml of methylacetate were mixed in a nitrogen atmosphere, and refluxed for 20 minutes to obtain acetylcyclopentadienyl sodium. To the solution containing colorless crystals thereby obtained, 40 ml of benzene was added, and 10.6 g of tris-triphenylphosphine cobalt monochloride was further added whereby a red solution of bistriphenylphosphine-$\eta^5$-acetylcyclopentadienyl cobalt was immediately obtained. The solution was stirred at room temperature for about 1 hour. Then, an aqueous ammonium chloride solution was added to remove the excess acetylcyclopentadienyl sodium by transferring it to the aqueous phase. The organic phase was dried over sodium sulfate and then filtered. To the solution thereby obtained, 5 ml of 1,5-cyclooctadiene was added, and the mixture was refluxed for 1 hour on a hot water bath, and then concentrated under reduced pressure. The product was subjected to alumina column chromatography, whereupon an orange brown fraction eluted by a mixture of benzene/hexane (1:1) was isolated. The solvent was distilled off, and the product was recrystallized from benzene/hexane to obtain 0.32 g of brown crystals.

(iii) Preparation of $\eta^4$-1,5-cyclooctadiene-$\eta^5$-1,3l-dimethoxycarbonylcyclopentadienylcobalt and the 1,2-dimethoxycarbonyl substituted isomer.

To a tetrahydrofuran solution of methoxycarbonyl cyclopentadienyl sodium (28 mmol/28 mol) prepared by the Rausch method, a tetrahydrofuran solution of methyl chloroformate (2g/30 ml) was added under cooling with ice. When the solution reached room temperature, it was filtered and concentrated under reduced pressure. Then, methylene chloride was added thereto to precipitate slightly pink precipitates. The precipitates were collected by filtration and dried to obtain 1.23 g of dimethoxycarbonylcyclopentadienyl sodium.

This solid (0.6 g) was dissolved in water, and mixed with a suspension of tris-triphenylphosphine cobalt monochloride in benzene (1.76 g, 2 ml), whereby the benzene phase turned reddish brown. To this mixed solution, 1,5-cyclooctadiene (2 ml) was added and mixed for 2 hours. Then, the organic phase was separated and dried over sodium sulfate, and filtered through a short alumina column. The solution was concentrated by heating under reduced pressure to remove the solvent, and the precipitated triphenylphosphine was removed by decantation. The solution was subjected to alumina chromatography. The solvent was distilled off under reduced pressure from two types of yellow fractions eluted by benzene/hexane (1:1), and the residue was dissolved in hexane under heating, and then left to stand in a refrigerator, whereupon reddish brown crystals were obtained. (Total amount: 360 mg, yield: 52%, production ratio 1:3.5)

TABLE 1

| Examples | Complex Nos. | Feed material I Substituted cyclopentadienyl complexes | Amounts m mol | Amounts of feed material II Tris-triphenyl phosphine Co halogenide | Feed material III Polyenes or acetylenes | Amounts | Reaction temp. °C. | Reaction time | Alumina column chromatography | States of complexes | Yields | Notes |
|---|---|---|---|---|---|---|---|---|---|---|---|---|
| 1 | C-1 | Methoxycarbonyl cyclopentadienyl sodium | 14 | 10 m mol | Norbornadiene | 3 ml | 78 | 1 hr | Benzene/hexane 1:1 | Reddish brown crystals | 2.0 g | |
| 2 | C-2 | Methoxycarbonyl cyclopentadienyl sodium | 7 | 4 | 1,5-Cyclooctadiene | 2 ml | RT | 24 hr | Benzene/hexane 1:1 | Reddish brown crystals | 0.45 g | |
| 3 | C-3 | Methoxycarbonyl cyclopentadienyl cobalt-bistriphenyl phosphine | | 5 | Cyclooctatetraenene | 1 ml | 78 | 1 hr | Benzene/hexane 2:1 | Reddish brown crystals | 0.46 g | |
| 4 | C-4 | Methoxycarbonyl cyclopentadienyl cobalt-bistriphenyl phosphine | | 2.5 | Butadiene | * | RT | 24 hr | Benzene/hexane 1:1 | Dark red crystals | 0.25 g | *Vapour phase was flushed with butadiene |
| 5 | C-5 | Methoxycarbonyl cyclopentadienyl cobalt-bistriphenyl phosphine | | 5 | Diphenylacetylene | 1.78 g (10 m mol) | RT | 24 hr | Benzene/hexane 2:1 | Dark brown crystals | 1.6 g | |
| 6 | C-6 | Methoxycarbonyl cyclopentadienyl cobalt-bistriphenyl phosphine | | 4 | Acetylene | * | RT | 10 min | Benzene | Green crystals | 0.05 g | *Vapour phase was flushed with acetylene |
| 7 | C-7 | (Methoxycarbonyl, methyl cyclopentadienyl) sodium | 6 | 4 | 1,5-Cyclooctadiene | 2 ml | 78 | 1 hr | *Benzene/hexane 1:2 | Brown crystals | 0.08 g | *Silica gel chromatography C-7 and C-8 formed simultaneously C-7/C-8 = ⅔ |
| 8 | C-8 | (Methoxycarbonyl, methyl cyclopentadienyl) sodium | 7 | 5 | Diphenylacetylene | 2 g | RT | 1 week | *Benzene/hexane 2:1 | Dark brown crystals* | 0.12 g | *Mixture of C-9 and C-10 C-9/C-10 = ⅓ Again subjected to charomatography to isolate C-9 |
| | C-9 | | | | | | | | Benzene/hexane 1:1 | Brown crystals | 1.69 g | |
| | C-10 | | | | | | | | | | | |
| 9 | C-11 | (Methoxycarbonyl, benzyl cyclopentadienyl)sodium | 6 | 4 | 1,5-Cyclooctadiene | 2 ml | 100 | 1 hr | | (Hardly crystallized) | | Used as the solution |
| 10 | C-12 | (Methoxycarbonyl, phenyl cyclopentadienyl)lithium | 6 | 4 | 1,5-Cyclooctadiene | 2 ml | 100 | 1 hr | Benzene/hexane 1:1 | Orange brown crystals | 0.32 g | |
| 11 | C-13 | Acetyl cyclopentadienyl sodium | 20 | 12 m mol | 1,5-Cyclooctadiene | 5 ml | 78 | 1 hr | Benzene/hexane 1:1 | Dark brown crystals | 0.05 g | |
| | C-14 | Formyl cyclopentadienyl sodium | 10 | 5 | " | 3 ml | RT | 24 hr | | Reddish | | |
| 12 | C-15 | Acetyl cyclopenta- | 20 | 12 | Norbornadiene | 3 | 78 | 1 | Benzene/hexane | | 0.18 g | |

TABLE 1-continued

| Examples | Complex Nos. | Feed material I Substituted cyclopentadienyl complexes | Amounts m mol | Amounts of feed material II Tris-triphenyl phosphine Co halogenide | Feed material III Polyenes or acetylenes | Amounts | Reaction temp. °C. | Reaction time | Alumina column chromatography | States of complexes | Yields | Notes |
|---|---|---|---|---|---|---|---|---|---|---|---|---|
| | | dienyl sodium | | | | ml | | hr | 1:1 | brown needle-like crystals | | |
| 13 | C-16 | Acetyl cyclopentadienyl lithium | 5 | 5 | Diphenyl acetylene | 0.9 g | RT | 5 hr | Benzene/hexane 1:1 | Dark green crystals | 0.64 g | |
| 14 | C-17 | Triphenylphosphine-η²-diphenyl acetylene-η⁵-acetyl cyclopentadienyl cobalt | | 0.15 g | " | 0.05 g | RT | 24 hr | Benzene 1:1 | Dark green crystals | 0.15 g | |
| 15 | C-18 | Acetyl methyl cyclopentadienyl cobalt | 20 | 12 | 1,5-Cyclopentadiene | 5 ml | 78 | 1 hr | Benzene/hexane 1:1 | Reddish brown oil | 0.62 g | Mixture of two isomers |
| 16 | C-19 C-20 | Dimethoxycarbonyl cyclopentadienyl sodium | 8 | 3.5 | " | 1 ml | RT | 24 hr | Benzene/hexane 1:1 | Reddish brown crystals | 0.06 g 0.11 g | C-19 and C-20 formed simultaneously |
| 17 | C-21 C-22 | Dimethoxycarbonyl cyclopentadienyl sodium | 8 | 3.5 | Norbornadiene | 2 ml | RT | 24 hr | Benzene/hexane 1:1 | Reddish brown crystals | 0.14 g 0.14 g | C-21 and C-22 formed simultaneously |
| 18 | C-23 | Dimethoxycarbonyl cyclopentadienyl sodium | 8 | 3.5 | Indene | 2 g | RT | 24 hr | Benzene/hexane 1:1 | Reddish brown oil | 0.16 g | |
| 19 | C-26 | Acetyl, benzyl cyclopentadienyl sodium | 3 | 2.5 mmol | 1,5-Cyclooctadiene | 2 ml | RT | 24 hr | | Reddish brown viscous oil | 0.09 g | Used as the solution |
| 20 | C-27 | Acetyl, phenyl cyclopentadienyl sodium | 3 | 2.5 | " | 2 ml | RT | 24 hr | | | | Used as the solution |
| 21 | C-28 | Propionyl cyclopentadienyl sodium | 3 | 2.5 | Diphenyl acetylene | 0.5 g | RT | 24 hr | | | | Used as the solution |
| 22 | C-29 | Acetyl, dimethyl cyclopentadienyl sodium | 3 | 2.5 | Norbornadiene | 2 ml | RT | 24 hr | | | | Used as the solution |
| 23 | C-31 | Methoxycarbonyl cyclopentadienyl sodium | 3 | 2.5 | Methyl phenylpropynoate | 0.5 g | RT | 0.5 hr | Benzene | Dark brown crystals | 1.13 g | Used as the solution |
| 24 | C-32 | Methoxycarbonyl cyclopentadienyl | 3 | 2.5 | Phenyl propynonitrile | 0.5 g | RT | 1 hr | | | | Used as the solution |

TABLE 1-continued

| Examples | Complex Nos. | Feed material I Substituted cyclopentadienyl complexes | Amounts m mol | Amounts of feed material II Tris-triphenyl phosphine Co halogenide | Feed material III Polyenes or acetylenes | Amounts | Reaction temp. °C | Reaction time | Alumina column chromatography | States of complexes | Yields | Notes |
|---|---|---|---|---|---|---|---|---|---|---|---|---|
| | | sodium | | | | | | | | | | |

C-1: $\eta^4$-Norbornadiene-$\eta^5$-methoxycarbonyl cyclopentadienyl cobalt
C-2: $\eta^4$-1,5-Cyclooctadiene-$\eta^5$-methoxycarbonyl cyclopentadienyl cobalt
C-3: $\eta^4$-Cyclooctatetraene-$\eta^5$-methoxycarbonyl cyclopentadienyl cobalt
C-4: $\eta^4$-Butadiene-$\eta^5$-methoxycarbonyl cyclopentadienyl cobalt
C-5: Triphenylphosphine-($\eta^5$-methoxycarbonyl cyclopentadienyl)tetraphenyl cobaltacyclopentadiene
C-6: [$\eta^5$-Methoxycarbonyl cyclopentadienyl-(cobaltacyclopentadiene)]-$\eta^5$-methoxycarbonyl cyclopentadienyl cobalt (Co-Co)
C-7: $\eta^4$-1,5-Cyclooctadiene-($\eta^5$-1-methoxycarbonyl, 3-methyl cyclopentadienyl)cobalt
C-8: $\eta^4$-1,5-Cyclooctadiene-($\eta^5$-1-methoxycarbonyl, 2-methyl cyclopentadienyl)cobalt
C-9: Triphenylphosphine-($\eta^5$-1-methoxycarbonyl, 2-methyl cyclopentadienyl)tetraphenylcobaltacyclopentadiene
C-10: Triphenylphosphine-($\eta^5$-1-methoxycarbonyl, 3-methyl, cyclopentadienyl)tetraphenylcobaltacyclopentadiene
C-11: $\eta^4$-1,5-Cyclooctadiene-($\eta^5$-methoxycarbonyl, benzylcyclopentadienyl)cobalt
C-12: $\eta^4$-1,5-Cyclooctadiene-($\eta^5$-methoxycarbonyl, phenylcyclopentadienyl)cobalt
C-13: $\eta^4$-1,5-Cyclooctadiene-$\eta^5$-acetylcyclopentadienyl cobalt
C-14: $\eta^4$-1,5-Cyclooctadiene-$\eta^5$-formylcyclopentadienyl cobalt
C-15: $\eta^4$-Norbornadiene-$\eta^5$-acetylcyclopentadienyl cobalt
C-16: Triphenylphosphine-$\eta^2$-diphenylacetylene-$\eta^5$-acetylcyclopentadienyl cobalt
C-17: Triphenylphosphine-($\eta^5$-acetylcyclopentadienyl)tetraphenylcobaltacyclopentadiene
C-18: $\eta^4$-1,5-Cyclooctadiene-($\eta^5$-acetyl, methyl cyclopentadienyl)cobalt
C-19: $\eta^4$-1,5-Cyclooctadiene-$\eta^5$-1,3-dimethoxycarbonyl cyclopentadienyl cobalt
C-20: $\eta^4$-1,5-Cyclooctadiene-$\eta^5$-1,2-dimethoxycarbonyl cyclopentadienyl cobalt
C-21: $\eta^4$-Norbornadiene-$\eta^5$-1,2-dimethoxycarbonyl cyclopentadienyl cobalt
C-22: $\eta^4$-Norbornadiene-$\eta^5$-1,3-dimethoxycarbonyl cyclopentadienyl cobalt
C-23: $\eta^4$-Indene-$\eta^5$-dimethoxycarbonyl cyclopentadienyl cobalt
C-26: $\eta^4$-1,5-Cyclooctadiene-($\eta^5$-acetyl, benzylcyclopentadienyl)cobalt
C-27: $\eta^4$-1,5-Cyclooctadiene-($\eta^5$-acetyl, phenylcyclopentadienyl)cobalt
C-28: Triphenylphosphine-($\eta^5$-propionylcyclopentadienyl)tetraphenylcobaltacyclopentadiene
C-29: $\eta^4$-Norbornadiene-($\eta^5$-acetyl, dimethylcyclopentadienyl)cobalt
C-31: Triphenylphosphine-($\eta^2$-methoxycarbonyl, phenylacetylene)-$\eta^5$-methoxycarbonyl cyclopentadienyl cobalt
C-32: Triphenylphosphine-($\eta^2$-cyano, phenylacetylene)-$\eta^5$-methoxycarbonylcyclopentadienyl cobalt

TABLE 2

| Complex Nos. | Melting point °C. | Values of elementary analysis [Theoretical values in ( )] C (%) | H (%) | IR absorption (Nujol) cm$^{-1}$ C=O | C=O | | NMR (in CDCl$_3$ or CD$_2$Cl$_2$), δ |
|---|---|---|---|---|---|---|---|
| C-1 | 50–51 | 61.27(61.32) | 5.52(5.51) | 1720 | 1700 | | 0.77  2.91  3.14  3.81  4.88  4.91<br>C$_7$H$_8$    CH$_3$    C$_5$H$_4$ |
| C-2 | 86–87 | 62.13(62.07) | 6.59(6.60) | 1720 | 1700 | | 1.63  2.38  3.58  3.95  4.40  5.03<br>C$_4$H$_8$    CH$_3$    C$_5$H$_4$ |
| C-3 | 67–68 | 62.84(62.95) | 5.25(5.28) | 1720 | 1700 | 1630 C=C | 3.64  5.56  3.90  4.55  5.11<br>C$_8$H$_8$    CH$_3$    C$_5$H$_4$ |
| C-4 | 40–42 | | | 1710 | | | 0.28  1.84  5.11  3.74  4.98  5.29<br>C$_4$H$_6$    CH$_3$    C$_5$H$_4$ |
| C-5 | 153–155 | 77.84(79.49) | 5.12(5.29) | 1720 | | | 6.4  7.4  3.82  4.69  5.43<br>C$_4$H$_4$    CH$_3$    C$_5$H$_4$ |
| C-6 | 68–70 | 51.94(51.95) | 4.34(4.36) | 1710 | 1695 | | 4.99  8.25   3.85  4.92  5.10<br>             3.90  5.52  5.58<br>C$_4$H$_4$    CH$_3$    C$_5$H$_4$ |
| C-7 | 63–64 | 63.20(63.16) | 6.92(6.96) | 1715 | | | 1.7, 2.4, 3.4  1.57   3.92   4.25  4.90<br>C$_8$H$_{12}$  C—CH$_3$  O—CH$_3$  C$_5$H$_4$ |
| C-8 | 47–49 | 63.06(63.16) | 6.90(6.96) | 1715 | | | 1.7  2.4   1.92   3.88   4.17  4.33<br>3.24  3.56                    5.02<br>C$_8$H$_{12}$  C—CH$_3$  O—CH$_3$  C$_5$H$_4$ |
| C-9<br>C-9<br>C-10 mixture | 136–138 | 79.62(79.60) | 5.42(5.44) | 1715 | 1725 | | C-9 { 1.63  C—CH$_3$   4.95  5.55<br>      3.26  O—CH$_3$   C$_5$H$_3$<br>C-10 { 1.40  C—CH$_3$   4.60  5.35<br>       3.64  O—CH$_3$   C$_5$H$_3$ |
| C-13 | 104–106 | 65.70(65.69) | 6.94(6.98) | 1660 | | | 1.66  2.40  3.55  2.70  4.20  5.20<br>C$_8$H$_{12}$    CH$_3$    C$_5$H$_4$ |
| C-14 | 158–160 | 64.61(64.62) | 6.62(6.59) | 1675 | 1650 | | 1.7  2.4  3.6  10.2  4.1  5.3<br>C$_8$H$_{12}$    CHO    C$_5$H$_4$ |
| C-15 | 97–99 | 65.49(65.12) | 5.85(5.86) | 1645 | | | 0.81  2.96  3.18   4.60  5.17<br>C$_7$H$_8$         C$_5$H$_4$ |
| C-16 | 133 | 77.89(77.22) | 5.41(5.32) | 1650 | 1655 | 1830<br>1835<br>C≡C | |
| C-17 | 164–165 | 80.98(81.11) | 5.61(5.39) | 1678 | | | 2.42  4.75  5.28<br>CH$_3$    C$_5$H$_4$ |
| C-19 | 115–116 | 58.71(58.63) | 6.09(6.08) | 1710 | 1725 | | 1.7  2.4  3.6  3.96  5.54  4.92<br>C$_8$H$_{12}$    CH$_3$    C$_5$H$_3$ |

TABLE 2-continued

| Complex Nos. | Melting point °C. | Values of elementary analysis [Theoretical values in ( )] | | IR absorption (Nujol) cm$^{-1}$ | | NMR (in CDCl$_3$ or CD$_2$Cl$_2$), δ |
|---|---|---|---|---|---|---|
| | | C (%) | H (%) | C = 0 | C = 0 | |
| C-20 | 99–100 | 58.67(58.63) | 6.12(6.08) | 1710 | 1730 | 1.7  2.4  3.6   3.85  4.94  5.16<br>     C$_8$H$_{12}$    CH$_3$    C$_5$H$_3$ |
| C-21 | 142–145 | | | | | 0.8  3.0  3.2   3.87  5.16  5.28<br>     C$_7$H$_8$    CH$_3$    C$_5$H$_3$ |
| C-22 | — | | | | | 0.8  3.0  3.2   3.83  5.00  5.10<br>     C$_7$H$_8$    CH$_3$    C$_5$H$_3$ |
| C-31 | 93–94 (decomp.) | 70.01(69.54) | 5.17(5.00) | — | — | 6.8  8.4  3.50  3.55  4.8  5.0<br>     C$_6$H$_5$    CH$_3$    C$_5$H$_4$ |

TABLE 3

| Complex Nos. | Structures |
|---|---|
| C-1 | CH$_3$OOC–[Cp]–Co–(norbornadiene) |
| C-2 | CH$_3$OOC–[Cp]–Co–(butadiene) |
| C-3 | CH$_3$OOC–[Cp]–Co–(cyclooctatetraene) |
| C-4 | CH$_3$OOC–[Cp]–Co–(cyclopentadiene) |
| C-5 | CH$_3$OOC–[Cp]–Co[(C$_6$H$_5$)$_3$P]–(tetraphenylcyclobutadiene with C$_6$H$_5$ substituents) |
| C-6 | CH$_3$OOC–[Cp]–Co—Co–[Cp]–COOCH$_3$ |

TABLE 3-continued
| Complex Nos. | Structures |
|---|---|
| C-7 | 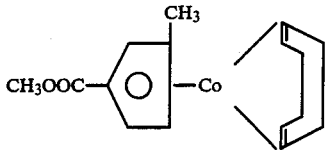 |
| C-8 | 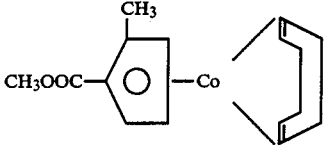 |
| C-9 | 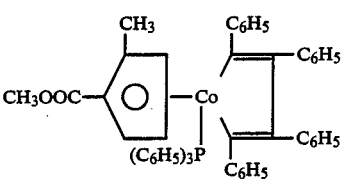 |
| C-10 | 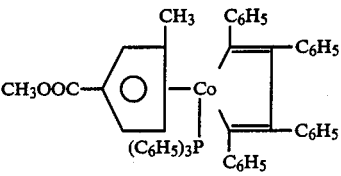 |
| C-11 | 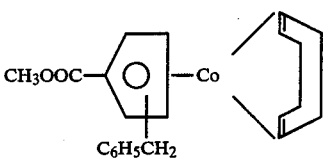 |
| C-12 | 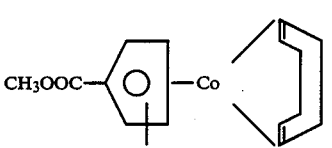 |
| C-13 | 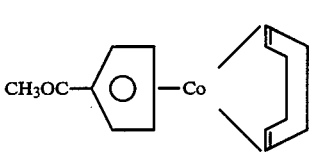 |
| C-14 | 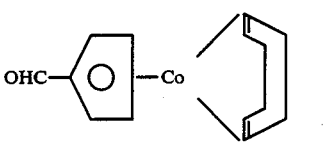 |
| C-15 | 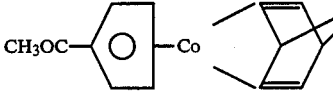 |

TABLE 3-continued

| Complex Nos. | Structures |
|---|---|
| C-16 | CH₃OC-[Cp]-Co(P(C₆H₅)₃)(C≡C-C₆H₅)₂ with alkyne C(C₆H₅)≡C(C₆H₅) |
| C-17 | CH₃OC-[Cp]-Co(P(C₆H₅)₃) with two C(C₆H₅)=C(C₆H₅) groups |
| C-18 | CH₃OC-[Cp-CH₃]-Co(cyclooctadiene) |
| C-19 | (CH₃OOC)₂-[Cp]-Co(cyclooctadiene) |
| C-20 | (CH₃OOC)₂-[Cp]-Co(cyclooctadiene) |
| C-21 | (CH₃OOC)₂-[Cp]-Co(norbornadiene) |
| C-22 | (CH₃OOC)₂-[Cp]-Co(norbornadiene) |
| C-23 | (CH₃OOC)₂-[Cp]-Co(indene) |
| C-24 | C₂H₅OOC-[Cp]-Co(cyclooctadiene) |

TABLE 3-continued

| Complex Nos. | Structures |
|---|---|
| C-25 | CH₃OOC—[Cp]—Co—[cyclohexenyl]—CH₂CN |
| C-26 | CH₃OC—[Cp(C₆H₅CH₂)]—Co—[COD] |
| C-27 | CH₃OC—[Cp(C₆H₅)]—Co—[COD] |
| C-28 | CH₃CH₂OC—[Cp(CH₃)]—Co(P(C₆H₅)₃)—[tetraphenylcyclobutadiene] |
| C-29 | CH₃OC—[Cp(CH₃, CH₃)]—Co—[norbornadiene] |
| C-30 | CH₃OC—[Cp(C₆H₅CH₂)]—Co—[norbornadiene] |
| C-31 | CH₃OOC—[Cp(CH₃)]—Co(P(C₆H₅)₃)—[C₆H₅, COOCH₃ alkene] |
| C-32 | CH₃OOC—[Cp(CH₃)]—Co(P(C₆H₅)₃)—[C₆H₅, CN alkene] |

EXAMPLES 25 TO 31

Table 4 shows examples for the preparation of complexes wherein a $\eta^5$-alkoxycarbonyl- or $\eta^5$-acylcyclopentadienyl alkali metal complex is reacted with a cobalt halide, and the reaction product was further reacted with a polyene in the presence of a reducing agent. The structures of the complexes thereby obtained are shown in Table 3. Typical methods for the preparation will be described below.

(i) Preparation of $\eta^4$-1,5-cyclooctadiene-$\eta^5$-methoxycarbonyl cyclopentadienylcobalt Into a 100 ml container, 1.0 g (7.7 mmol) of anhydrous cobalt chloride, 15 ml of tetrahydrofuran and 3 ml of 1,5-cyclooctadiene were introduced in a nitrogen stream. While stirring the mixture, 5 ml (7 mmol) of a tetrahydrofuran solution of methoxycarbonyl cyclopentadienyl sodium was dropwise added at 15° C. The non-uniform blue-colored mixed solution became dark red and uniform as the dropwise addition proceeded.

To a system prepared in another container comprising mercury amalgam of sodium (0.7 g of sodium) and 10 ml of tetrahydrofuran, the above solution was added at 15° C. under stirring. After stirring for 10 minutes, the supernatant was separated, and the solvent was distilled off under reduced pressure. The residue was dissolved in a small amount of benzene/hexane (1:1), and subjected to alumina column chromatography (5% of water was added). The eluted reddish brown fraction was collected and the solvent was distilled off, whereby the desired $\eta^4$-1,5-cyclooctadiene-$\eta^5$-methoxycarbonyl cyclopentadienylcobalt (the same substance as C-2) was obtained in the form of crystals. This product was washed with a small amount of hexane and dried under reduced pressure, whereupon 620 mg of the product was obtained.

TABLE 4

| Examples | Complex Nos. | Feed material I Substituted cyclopentadienyl complexes | Amounts m mol | Feed material III Polyenes or acetylenes | Amounts | Reducing agent | Reaction temp. °C. | Reaction time | Alumina column chromatography | States of complexes | Yields | Notes |
|---|---|---|---|---|---|---|---|---|---|---|---|---|
| 25 | C-2 | Methoxycarbonyl cyclopentadienyl sodium Cobalt(II)chloride | 7.0 7.7 | 1,5-Cyclooctadiene | 3 ml | Sodium-amalgam | 15 | 10 min | Benzene:hexane 1:1 | Reddish brown crystals | 0.62 g | |
| 26 | C-2 | Methoxycarbonyl cyclopentadienyl cobalt(mono) chloride | 4.0 | 1,5-Cyclooctadiene | 1.5 ml | Sodium borohydride | 0 | 1 hr | Benzene:hexane 1:1 | Reddish brown crystals | 0.14 g | |
| 27 | C-15 | Acetyl cyclopentadienyl sodium Cobalt(II)iodide | 7.0 7.0 | Norbornadiene | 4 ml | Sodium-amalgam | 0 *40 | 0.5 hr 15 min | Benzene:hexane 1:1 | Reddish brown crystals | 0.25 g | *On the reducing reaction |
| 28 | C-4 | Methoxycarbonyl cyclopentadienyl sodium Cobalt(II)chloride | 8.5 8.5 | Butadiene | * | Sodium-amalgam | 0 | 1 hr | Benzene:hexane 1:1 | Dark red crystals | 0.44 g | *A THF solution saturated with butadiene was added to the cobalt complex solution |
| 29 | C-25 | Methoxycarbonyl cyclopentadienyl sodium Cobalt(II)chloride | 3.0 3.0 | Cyanomethylene cyclopentadiene | 1.5 ml | Sodium-amalgam | 0 | 1 hr | | | | Used as the solution |
| 30 | C-24 | Ethoxycarbonyl cyclopentadienyl sodium Cobalt(II)chloride | 3.0 | 1,5-Cyclooctadiene | 1.5 ml | Sodium-amalgam | 0 | 0.5 hr | | | | Used as the solution |
| 31 | C-30 | Acetyl,benzyl cyclopentadienyl lithium Cobalt(II)chloride | 2.0 2.0 | Norbornadiene | 1.5 ml | Sodium-amalgam | 20 | 1 hr | | | | Used as the solution |

C-2: η⁴-1,5-Cyclooctadiene-η⁵-methoxycarbonyl cyclopentadienyl cobalt
C-15: η⁴-Norbornadiene-η⁵-acetylcyclopentadienyl cobalt
C-4: η⁴-1,3-Butadiene-η⁵-methoxycarbonyl cyclopentadienyl cobalt
C-25: η⁴-Cyanomethylenecyclopentadiene-η⁵-methoxycarbonyl cyclopentadienyl cobalt
C-24: η⁴-1,5-Cyclooctadiene-η⁵-ethoxycarbonyl cyclopentadienyl cobalt
C-30: η⁴-Norbornadiene-(η⁵-acetyl,benzylcyclopentadienyl)cobalt

EXAMPLE 32

Synthesis of 2-vinylpyridine

Into a 100 ml stainless steel autoclave, 76 mg (0.26 mmol) of $\eta^4$-1,5-cyclooctadiene-$\eta^5$-methoxycarbonyl-cyclopentadienylcobalt (C-2) prepared in Example 2 and dissolved in 60 ml of toluene was fed in an argon atmosphere, and 20 g of acrylonitrile was further fed. The autoclave was flushed with acetylene and heated to 150° C. from atmospheric pressure, and then acetylene was continuously supplied to maintain the pressure at 13 kg/cm²G. The reaction was continued for 60 minutes, whereby 2-vinylpyridine was synthesized. The reaction solution was analyzed by gas chromatography. The results are shown in Table 5. The concentration of 2-vinylpyridine in the reactant solution was 18%, and STY of the reaction reached 168 g/liter.hr.

EXAMPLES 33 TO 54

2-Vinylpyridine was synthesized in the same manner as in Example 32 by using different complexes. the reaction conditions and the results are shown in Table 5.

EXAMPLES 55 TO 67

2-Vinylpyridine was synthesized in the same manner as in Example 32 by using $\eta^4$-1,5-cyclooctadiene-$\eta^5$-methoxycarbonylcyclopentadienylcobalt and changing the reaction conditions. The results are shown in Table 6.

TABLE 5

| Example No | Catalyst No | Amounts of catalysts m mol | Solvents | Amounts of solvents ml | Amounts of acrylo-nitrile g | Acetylene pressure kg/cm² G | Reaction time min | Catalytic efficiency for vinyl pyridine *1 | Formation ratio of benzene by-product *2 | Notes |
|---|---|---|---|---|---|---|---|---|---|---|
| 32 | C-2 | 0.26 | Toluene | 60 | 20 | 13 | 60 | 529 | 0.05 | |
| 33 | C-1 | 0.23 | " | 54 | 17.8 | 13 | 60 | 140 | 0.05 | |
| 34 | C-5 | 0.07 | " | 80 | 5 | 13 | 60 | 368 | 0.17 | |
| 35 | C-24 | 0.23 | " | 54 | 17.8 | 13 | 60 | *³387 | 0.05 | |
| 36 | C-6 | 0.08 | " | 60 | 20 | 13 | 60 | 151 | 0.06 | |
| 37 | C-4 | 0.26 | " | 60 | 20 | 13 | 60 | 370 | 0.02 | |
| 38 | C-7 | 0.12 | " | 60 | 20 | 13 | 60 | 602 | 0.04 | |
| 39 | C-9 / C-10 | 0.12 | " | 60 | 20 | 13 | 60 | 391 | 0.04 | Mixture of C-9/C-10 at 1/3 |
| 40 | C-11 | 0.4 | " | 60 | 20 | 13 | 60 | *³179 | 0.04 | |
| 41 | C-12 | 0.4 | " | 60 | 20 | 13 | 60 | *³220 | 0.04 | |
| 42 | C-13 | 0.26 | " | 60 | 20 | 13 | 60 | 434 | 0.03 | |
| 43 | C-14 | 0.09 | " | 45 | 14.7 | 13 | 60 | 124 | 0.02 | |
| 44 | C-15 | 0.26 | " | 60 | 20 | 13 | 60 | 174 | 0.03 | |
| 45 | C-16 | 0.09 | " | 45 | 14.7 | 13 | 60 | 340 | 0.03 | |
| 46 | C-17 | 0.09 | " | 45 | 14.7 | 13 | 60 | 327 | 0.02 | |
| 47 | C-18 | 0.26 | " | 60 | 20 | 13 | 60 | *³260 | 0.03 | |
| 48 | C-25 | 0.26 | " | 60 | 20 | 13 | 60 | *³160 | 0.04 | |
| 49 | C-26 | 0.26 | " | 60 | 20 | 13 | 60 | *³195 | 0.04 | |
| 50 | C-27 | 0.02 | " | 30 | 10 | 13 | 60 | *³120 | 0.02 | |
| 51 | C-28 | 0.26 | " | 60 | 20 | 13 | 60 | 111 | 0.02 | |
| 52 | C-19 | 0.13 | " | 45 | 10 | 13 | 60 | 114 | 0.05 | |
| 53 | C-20 | 0.13 | " | 45 | 10 | 13 | 60 | 144 | 0.05 | |
| 54 | C-21 / C-22 | 0.23 | " | 54 | 17.8 | 13 | 60 | 130 | 0.04 | Mixture of C-21/C-22 at 1/1 |

TABLE 6

| Example Nos. | Catalyst Nos. | Amounts of catalysts m mol | Solvents | Amounts of solvents ml | Amounts of acrylo-nitrile g | Acetylene pressure kg/cm² G | Reaction time min | Catalytic efficiency for vinyl pyridine *1 | Formation ratio of benzene by-product *2 | Notes |
|---|---|---|---|---|---|---|---|---|---|---|
| 55 | C-2 | 0.26 | Toluene | 60 | 20 | 13 | 60 | 529 | 0.05 | |
| 56 | *⁴C-2 | 0.26 | " | 60 | 20 | 13 | 60 | *³422 | 0.03 | |
| 57 | C-2 | 0.05 | " | 60 | 4 | 13 | 60 | 734 | 0.14 | |
| 58 | C-2 | 0.26 | " | 60 | 20 | 5 | 60 | 90 | 0.01 | |
| 59 | C-2 | 3.9 | " | 1000 | 233 | 10 | 90 | 320 | 0.03 | Reaction temp. 130° C. |
| 60 | C-2 | 4.7 | " | 1000 | 233 | 10 | 60 | 141 | 0.04 | Reaction temp. 170° C. |
| 61 | C-2 | 3.0 | " | 1000 | 233 | 10 | 60 | 202 | 0.03 | |
| 62 | C-2 | 4.7 | " | 1000 | 233 | 10 | 120 | 296 | 0.04 | |
| 63 | C-2 | 3.0 | Benzene | 1000 | 233 | 10 | 60 | 177 | — | |
| 64 | C-2 | 3.0 | Octanol | 1000 | 233 | 10 | 60 | 125 | 0.03 | |
| 65 | C-2 | 3.0 | Decalin | 1000 | 233 | 10 | 60 | 198 | 0.04 | |
| 66 | C-2 | 3.0 | Diethyl aniline | 1000 | 233 | 10 | 60 | 117 | 0.05 | |
| 67 | C-2 | 3.0 | Dimethyl formamide | 1000 | 233 | 10 | 60 | 101 | 0.07 | |
| Comp. Exp. 1 | C-100 | 0.26 | Toluene | 80 | 5 | 13 | 60 | 89 | 0.26 | |
| Comp. Exp. 2 | C-101 | 0.26 | " | 80 | 5 | 13 | 60 | 83 | 0.29 | |

TABLE 9

| Example Nos. | Catalyst Nos. | Catalytic efficiency for pyridine Pyridine mol/Co g atom |
|---|---|---|
| 76 | C-2 | 46 |
| 77 | C-19 | 29 |
| 78 | C-20 | 45 |
| 79 | C-23 | 12 |
| 80 | C-24 | 40 |
| 81 | C-25 | 7.5 |
| 82 | C-30 | 10 |
| Comparative Example 5 | C-100 | trace |
| Comparative Example 6 | C-101 | trace |
| Comparative Example 7 | C-102 | trace |

EXAMPLE 83

26 mg (0.09 mmol) of $\eta^4$-1,5-cyclooctadiene-$\eta^5$-methoxycarbonylcyclopentadienylcobalt (C-2) as a cataylst, 10 g of phenyl acetylene, 20 g of acetonitrile and 50 ml of toluene were fed, and reacted at a temperature of 130° C. for 120 minutes.

The product was analyzed by liquid chromatography, whereby the production of 2-methyldiphenyl pyridines were found to be 2.24 g, and the catalytic efficiency was found to be 100 mol/Co g atom.

EXAMPLE 84

By using 76 mg of the same catalyst (C-2) as in Example 83, acetylene and benzonitrile were reacted. 20 g of benzonitrile and 60 ml of toluene were fed, and the reaction was conducted at a temperature of 130° C. for 60 minutes under pressure of 10 kg/cm²G.

The product was analyzed by gas chromatography, whereby it was found that 20.2 g of 2-phenylpyridine was obtained, and the catalytic efficiency was 458 mol/Co g atom.

EXAMPLE 85

Into a 100 ml pressure-resistant glass reactor, 30 mg (0.107 mmol) of $\eta^4$-cyclooctatetraene-$\eta^5$-methoxycarbonylcyclopentadienylcobalt (C-3) as a catalyst, 2.5 g of acetonitrile and 60 ml of toluene were fed. Then, while cooling the reactor, ethylacetylene was blown into the reactor in small portions, whereby about 10 ml of liquid ethylacetylene was condensed. The reactor was sealed and heated at 120° C. for 4 hours.

After cooling, reaction solution was analyzed by gas chromatography, whereby it was found that 0.72 g of 2-methyldiethyl pyridines were obtained, and the catalytic efficiency was 44 mol/Co g atom.

EXAMPLE 86

The reaction was conducted in the same manner as in Example 85 except that 25 mg (0.104 mmol) of $\eta^4$-butadiene-$\eta^5$-methoxycarbonylcyclopentadienylcobalt was used as the catalyst.

As the result, 0.47 g of 2-methyldiethyl pyridines were obtained, and the catalytic efficiency was 30 mol/Co g atom.

We claim:

1. In a process for preparing a pyridine homologue, which comprises reacting an alkyne with a nitrile in the presence of a cobalt-containing complex, the improvement which comprises conducting said reaction in the presence of a complex of an electron attracting group-substituted $\eta^5$-cyclopentadienylcobalt comprising a polyene or an acetylene, which is represented by the general formula

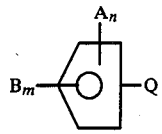

wherein A is a $C_1$-$C_4$ alkyl group or a phenyl group; n is an integer of from 0 to 2, B is an alkoxycarbonyl group in which the alkoxy moiety contains from 1 to 3 carbon atoms or a $C_1$-$C_4$ acyl group, m is an integer of 1 or 2, and Q is —Co=$R_1$ where $R_1$ is a $\eta^4$ $C_4$-$C_{12}$ polyene having from 2 to 4 double bonds, which is unsubstituted or substituted by from 1 to 4 substituents selected from the group consisting of a $C_1$-$C_4$ alkyl group and a $C_1$-$C_4$ alkoxycarbonyl group, and which forms a coordinate bond with the cobalt atom at its diene portion, provided $R_1$ excludes a polyene composed solely of an aromatic ring,

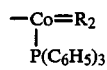

where $R_2$ is an organic residue of a metallo-cyclic cyclopentadiene composed of two molecules of an acetylene which may be unsubstituted or substituted by from 1 to 4 substituents selected from the group consisting of a $C_1$-$C_4$ alkyl group, a $C_1$-$C_4$ alkoxycarbonyl group, a phenyl group and a cyano group,

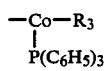

where $R_3$ is an acetylene which is substituted by one or two substituents selected from the group consisting of a $C_1$-$C_4$ alkyl group, a $C_1$-$C_4$ alkoxycarbonyl group, a phenyl group and a cyano group and which forms a coordinate bond with the cobalt atom at its triple bond portion, and

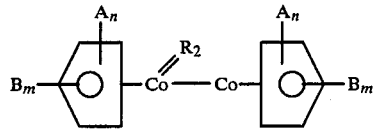

where A, B, n, m and $R_2$ are as defined as above.

2. The process according to claim 1, wherein the complex is selected from the group consisting of complexes represented by the formula:

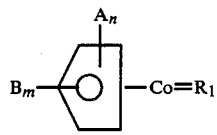

(II)

where A, n, m and $R_1$ are as defined in claim 1, and B is an alkoxycarbonyl group in which the alkoxy moiety contains from 1 to 3 carbon atoms:

TABLE 6-continued

| Example Nos. | Catalyst Nos. | Amounts of catalysts m mol | Solvents | Amounts of solvents ml | Amounts of acrylonitrile g | Acetylene pressure kg/cm² G | Reaction time min | Catalytic efficiency for vinyl pyridine *1 | Formation ratio of benzene by-product *2 | Notes |
|---|---|---|---|---|---|---|---|---|---|---|
| Exp. 3 | C-102 | 0.26 | " | 80 | 5 | 13 | 60 | 102 | 0.26 | |

*1Catalytic efficiency = vinyl pyridine mol/Co g atom
*2Formation ratio of benzene by-product = Benzene mol/vinyl pyridine mol
*3The reacton solution obtained by the preparation of the complex was used by itself as a catalyst solution. The catalytic efficiency is represented by a value based on the total cobalt concentration in the solution.
*4The reaction product solution obtained in Example 25 (i.e. the supernatant after the sodium amalgam treatment) was used by itself.

COMPARATIVE EXAMPLES 1 TO 3

The same operation as in Example 57 was conducted by using conventional catalyst. As the catalyst, biscyclopentadienyl cobalt (C-100), $\eta^4$-1,5-cyclooctadiene-$\eta^5$-cyclopentadienylcobalt (C-101) and $\eta^4$-1-exo-cyanomethylene cyclopentadiene-$\eta^5$-cyclopentadienyl cobalt (C-102) were used. The results thereby obtained are shown in Table 6.

It is evident that the complexes prepared in Examples 1 to 31 have high catalytic activities, whereby the formation of benzene as a by-product is minimum.

EXAMPLES 68 TO 71

Into a 100 ml stainless steel autoclave, 24 mg (0.087 mmol) of $\eta^4$-1,5-cyclooctadiene-$\eta^5$-acetylcyclopentadienyl cobalt as a catalyst and 66.6 g of acetonitrile were fed in an argon atmosphere, and reacted at a temperature of 150° C. for 60 minutes under acetylene pressure of 13 kg/cm²G to obtain α-picoline. Similar reactions were conducted by using other complexes identified in Table 7.

TABLE 7

| Example Nos. | Catalyst Nos. | Catalytic efficiency for α-picoline α-Picoline mol/ Co g atom | Formation ratio of benzene by-product Benzene/α-picoline | Notes |
|---|---|---|---|---|
| 68 | C-13 | 1093 | 0.02 | |
| 69 | C-9 | 330 | 0.02 | Mixture of C-9/C-10 at ½ |
| | C-10 | | | |
| 70 | C-2 | 1140 | 0.02 | The reaction solution obtained in Example 25 was used by itself as the catalyst. |
| 71 | C-24 | 870 | 0.02 | |

EXAMPLES 72 TO 75

A predetermined amount of a complex, 12 ml of benzene, 12 ml of acetonitrile and about 4 g of methyl acetylene were sealed in an ampoule, and heated to 95° C. and reacted for 29 hours. The results are shown in Table 8.

TABLE 8

| Example Nos. | Catalyst Nos. | Amounts of catalysts | Catalytic efficiency 2,3,6-Trimethyl pyridine | Catalytic efficiency 2,4,6-Trimethyl pyridine | Formation ratio of trimethyl benzene by-product | Notes |
|---|---|---|---|---|---|---|
| 72 | C-2 | 0.025 | 564 | 580 | 0.13 | |
| 73 | C-19 | 0.025 | 372 | 398 | 0.21 | Mixture of C-19/C-20 at 1/1 |
| | C-20 | | | | | |
| 74 | C-31 | 0.04 | 258 | 297 | 0.17 | |
| 75 | C-32 | 0.04 | 285 | 250 | 0.25 | The solution was used by itself |
| Comparative Exp. 4 | C-101 | 0.05 | 103 | 148 | 0.22 | |

EXAMPLES 76 TO 82

Acetylene and hydrogen cyanide were reacted in the same manner as in Example 32. 0.26 mmol of the complex, 2.5 ml of hydrogen cyanide and 43 ml of toluene were fed, and the reaction was conducted at a temperature of 150° C. for 62 minutes under pressure of from 15 to 18 kg/cm²G. The resulting pyridine was analyzed by gas chromatography. The results are shown in Table 9.

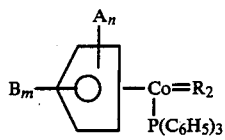

(III)

wherein A, n, m and $R_2$ are as defined in claim 1, and B is an alkoxycarbonyl group in which the alkoxy moiety contains from 1 to 3 carbon atoms:

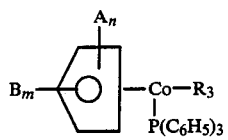

(IV)

wherein A, n, m and $R_3$ are as defined in claim 1, and B is an alkoxycarbonyl group in which the alkoxy moiety contains from 1 to 3 carbon atoms:

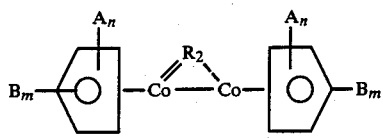

(V)

where A, B, n, m, and $R_2$ are as defined above.

3. The process for preparing a pyridine homologue in the presence of a catalyst according to claim 2, which is carried out in the presence of a catalyst consisting of the complex or a solution having the complex which is prepared by reacting an alkoxycarbonyl-substituted cyclopentadienyl alkali metal complex which has 1 to 3 carbon atoms in the alkoxy moiety, with a tris-triphenyl-phosphine cobalt monohalide, and reacting a bis-triphenyl-phosphine complex of the alkoxycarbonyl-substituted cyclopentadienylcobalt having 1 to 3 carbon atoms in the alkoxy moiety thereby obtained, with a polyene or an acetylene.

4. The process for preparing a pyridine homologue according to claim 2, which is carried out in the presence of a catalyst consisting of the complex of the formula II or a solution having the complex of the formula II, which is prepared by reacting an alkoxycarbonyl-cyclopentadienylcobalt monohalide having from 1 to 3 carbon atoms in the alkoxy moiety, with a polyene in the presence of a reducing agent which is an alkali metal amalgam, hydride, borohydride or aluminum hydride, an alkyl aluminum or an alkyl zinc.

5. The process for preparing a pyridine homologue according to claim 2, which is carried out in the presence of a catalyst consisting of the complex of the formula II or a solution having the complex of the formula II which is prepared by reacting an alkoxycarbonyl-cyclopentadienyl alkali metal complex having from 1 to 3 carbon atoms in the alkoxy moiety, with a cobalt(II) halide, and then reacting the resulting alkoxycarbonyl-cyclopentadienylcobalt monohalide having from 1 to 3 carbon atoms in the alkoxy moiety, with a polyene in the presence of a reducing agent which is an alkali metal amalgam, hydride, or borohydride or aluminium hydride, an alkyl aluminum or an alkyl zinc.

6. The process according to claim 2, wherein the nitrile is hydrogen cyanide, an alkyl-, aryl- or alkenyl-nitrile, or a polyfunctional nitrile wherein a plurality of nitrile groups are bonded to the alkyl-, aryl- or alkenyl-nitrile.

7. The process according to claim 2, wherein a hydrocarbon, an alcohol, an amine, an ester or an alkylcarboxyamide is used as a solvent.

8. The process according to claim 2, wherein the starting material nitrile is used as a solvent.

9. The process according to claim 2, wherein the complex is present in the reaction system in an amount of from 0.1 to 100 mmol/liter.

10. The process according to claim 2, wherein the molar ratio of the alkyne to the nitrile is within a range of from 0.01 to 100.

11. The process according to claim 2, wherein the reaction is conducted at a temperature of from 15° to 200° C.

12. The process according to claim 2, wherein acetylene and acrylonitrile are reacted to form 2-vinyl pyridine.

13. The process according to claim 2, wherein acetylene and acetonitrile are reacted to form α-picoline.

14. The process according to claim 2, wherein the alkyne is unsubstituted acetylene or acetylene substituted by an alkyl, alkenyl, aryl, dialkyl, diaryl, alkylalkenyl, alkylaryl, ether or alcohol, or a mixture thereof.

15. The process according to claim 12, wherein the partial pressure of acetylene is from 0 to 30 kg/cm²G.

16. The process according to claim 13, wherein the partial pressure of acetylene is from 0 to 30 kg/cm²G.

17. The process for preparing a pyridine homologue according to claim 1, which is carried out in the presence of a catalyst consisting of the complex or a solution having the complex, which is prepared by reacting a $C_1$-$C_4$ acyl substituted cyclopentadienyl alkali metal complex with a tris-triphenyl-phosphine cobalt monohalide, and reacting a bis-triphenylphosphine complex of the $C_1$-$C_4$ acyl-substituted cyclopentadienyl-cobalt thereby obtained, with a polyene or an acetylene.

18. The process for preparing a pyridine homologue according to claim 1, which is carried out in the presence of a catalyst consisting of the complex or a solution having the complex of the formula II, which is prepared by reacting a $C_1$-$C_4$ acylcyclopentadienylcobalt monohalide with a polyene in the presence of a reducing agent which is an alkali metal amalgam, hydride, borohydride or aluminum hydride, an alkyl aluminum or an alkyl zinc.

19. The process for preparing a pyridine homologue according to claim 1, which is carried out in the presence of a catalyst consisting of the complex or a solution having the complex, which is prepared by reacting a $C_1$-$C_4$ acyl-cyclopentadienyl alkali metal complex with a cobalt(II) halide and then reacting the resulting $C_1$-$C_4$ acyl-cyclopentadienylcobalt monohalide with a polyene in the presence of a reducing agent which is an alkali metal amalgam, hydride, borohydride or aluminum hydride, an alkyl aluminum or an alkyl zinc.

20. The process according to claim 1, wherein the nitrile is hydrogen cyanide, an alkyl-, aryl- or alkenyl-nitrile, or a polyfunctional nirtrile wherein a plurality of nitrile groups are bonded to the alkyl-, aryl- or alkenyl-nitrile.

21. The process according to claim 1, wherein a hydrocarbon, an alochol, an amine, an ester or an alkylcarboxyamide is used as a solvent.

22. The process according to claim 1, wherein the starting material nitrile is used as a solvent.

23. The process according to claim 1, wherein the complex is present in the reaction system in an amount of from 0.1 to 100 mmol/liter.

24. The process according to claim 1, wherein the molar ratio of the alkyne to the nitrile is within a range of from 0.01 to 100.

25. The process according to claim 1, wherein the reaction is conducted at a temperature of from 15° to 200° C.

26. The process according to claim 1, wherein acetylene and acrylonitrile are reacted to form 2-vinyl pyridine.

27. The process according to claim 26, wherein the partial pressure of acetylene is from 0 to 30 kg/cm$^2$G.

28. The process according to claim 1, wherein acetylene and acetonitrile are reacted to form $\alpha$-picoline.

29. The process according to claim 28, wherein the partial pressure of acetylene is from 0 to 30 kg/cm$^2$G.

30. The process according to claim 1, wherein the alkyne is unsubstituted acetylene or acetylene substituted by an alkyl, alkenyl, aryl, dialkyl, diaryl, alkylalkenyl, alkylaryl, ether or alcohol, or a mixture thereof.

31. The process according to claim 1, wherein the complex is selected from the group consisting of complexes represented by the formula:

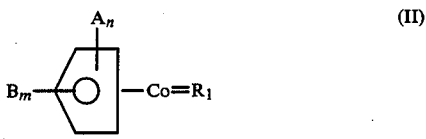
(II)

wherein A, n, m and $R_1$ are as defined in claim 1, and B is a $C_1$–$C_4$ acyl group:

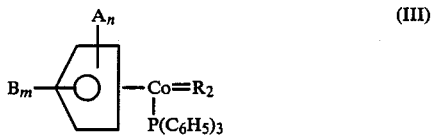
(III)

wherein A, n, m and $R_2$ are defined in claim 1, and B is a $C_1$–$C_4$ acyl group:

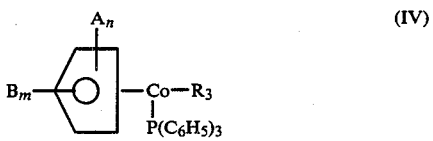
(IV)

wherein A, n, m, and $R_3$ are as defined in claim 1, and B is a $C_1$–$C_4$ acyl group:

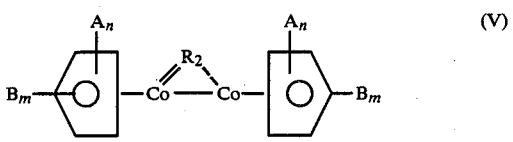
(V)

where A, B, n, m and $R_2$ are as defined above.

32. The process according to claim 3, wherein a $C_4$–$C_{12}$ polyene having from 2 to 4 double bonds, which is unsubstituted or substituted by from 1 to 4 substituents selected from the group consisting of a $C_1$–$C_4$ alkyl group, a $C_1$–$C_4$ alkoxycarbonyl group, a phenyl group, a cyano grop and a cyanomethylene group, is used as the polyene to form the complex of the formula II.

33. The process according to claim 3, wherein acetylene which is unsubstituted or substituted by one or two substituents selected from the group consisting of a $C_1$–$C_4$ alkyl group, a $C_1$–$C_4$ alkoxycarbonyl group, a phenyl group and a cyano group, is reacted in a ratio of two molecules to one cobalt atom to form the complex of the formula III.

34. The process according to claim 3, wherein acetylene which is unsubstituted or substituted by one or two substituents selected from the group consisting of a $C_1$–$C_4$ alkyl group, a $C_1$–$C_4$ alkoxycarbonyl group, a phenyl group and a cyano group, is reacted in a ratio of one molecule to one cobalt atom to form the complex of the formula IV.

35. The process according to claim 3, wherein the complex of the formula III is further reacted with a substituted $\eta^5$-cyclopentadienylcobalt bis-triphenylphosphine complex to form the complex of the formula V.

36. The process according to claim 3, wherein a substituted $\eta^5$-cyclopentadienylcobalt bis-triphenylphosphine complex is reacted with an unsubstituted or substituted acetylene to form the complex of the formula V.

37. The process according to claim 17, wherein a $C_4$–$C_{12}$ polyene having from 2 to 4 double bonds, which is unsubstituted or substituted by from 1 to 4 substituents selected from the group consisting of a $C_1$–$C_4$ alkyl group, a $C_1$–$C_4$ alkoxycarbonyl group, a phenyl group, a cyano group and a cyanomethylene group, is used as the polyene to form the complex of the formula II.

38. The process according to claim 17, wherein acetylene which is unsubstituted or substituted by one or two substituents selected from the group consisting of a $C_1$–$C_4$ alkyl group, a $C_1$–$C_4$ alkoxycarbonyl group, a phenyl group and a cyano group, is reacted in a ratio of two molecules to one cobalt atom to form the complex of the formula III.

39. The process according to claim 17, wherein acetylene which is unsubstituted or substituted by one or two substituents selected from the group consisting of a $C_1$–$C_4$ alkyl group, a $C_1$–$C_4$ alkoxycarbonyl group, a phenyl group and a cyano group, is reacted in a ratio of one molecule to one cobalt atom to form the complex of the formula IV.

40. The process according to claim 17, wherein the complex of the formula III is further reacted with a substituted $\eta^5$-cyclopentadienylcobalt bis-triphenylphosphine complex to form the complex of the formula V.

41. The process according to claim 17, wherein a substituted $\eta^5$-cyclopentadienylcobalt bis-triphenylphosphine complex is reacted with an unsubstituted or substituted acetylene to form the complex of the formula V.

* * * * *